United States Patent [19]

Leichnitz et al.

[11] Patent Number: 5,093,269
[45] Date of Patent: Mar. 3, 1992

[54] PROCESS AND ARRANGEMENT FOR DETERMINING AT LEAST ONE COMPONENT OF A TEST GAS

[75] Inventors: Kurt Leichnitz, Gross Grönau; Hans Matthiessen, Gross Parin, both of Fed. Rep. of Germany

[73] Assignee: Drägerwerk Aktiengesellschaft, Lübeck, Fed. Rep. of Germany

[21] Appl. No.: 116,640

[22] Filed: Nov. 3, 1987

[30] Foreign Application Priority Data

Dec. 12, 1986 [DE] Fed. Rep. of Germany ....... 3643804

[51] Int. Cl.$^5$ .............................................. G01N 1/18
[52] U.S. Cl. ..................................... 436/178; 422/88; 73/23.42; 73/863.12
[58] Field of Search .................. 422/88; 73/23, 863.11, 73/863.12, 23.1; 340/632; 324/71.1 R; 55/205, 179; 436/178

[56] References Cited

U.S. PATENT DOCUMENTS

| | | | |
|---|---|---|---|
| 4,073,620 | 2/1978 | Gray et al. | 422/88 |
| 4,277,251 | 7/1981 | Leichnitz et al. | 422/88 X |
| 4,515,751 | 5/1985 | Krieg | 422/86 |
| 4,759,210 | 7/1988 | Wohltjen | 73/23 |
| 4,912,051 | 3/1990 | Zaromb | 422/88 X |

OTHER PUBLICATIONS

Kindlund, A. et al., "Quartz Crystal Gas Monitor with a Gas Concentrating Stage", *Sensors and Actuators*, 6 (1984), 1–17.

Primary Examiner—David L. Lacey
Assistant Examiner—Jeffrey R. Snay
Attorney, Agent, or Firm—McGlew & Tuttle

[57] ABSTRACT

A process for determination of one component of very low concentration in a test gas, which is guided in a supply line for concentration of the component across a sample collector, whose amassed quantity of samples is relinquished to a detection sensor. The arrangement makes available a measurement signal even during the collection of the sample. It also makes even the individual components of a multicomponent test gas detectable and a component-specific cross sensitivity of the detection sensor controllable. For this, the following process steps are provided: the test gas is first guided across the detection sensor 3 and then across the multistaged sample collector 7 having arrangements for separation of the several components; then after interruption of the supply of test gas, each individual stage 4, 5 and 6 separately relinquishes its separated component to the detection sensor 3.

4 Claims, 1 Drawing Sheet

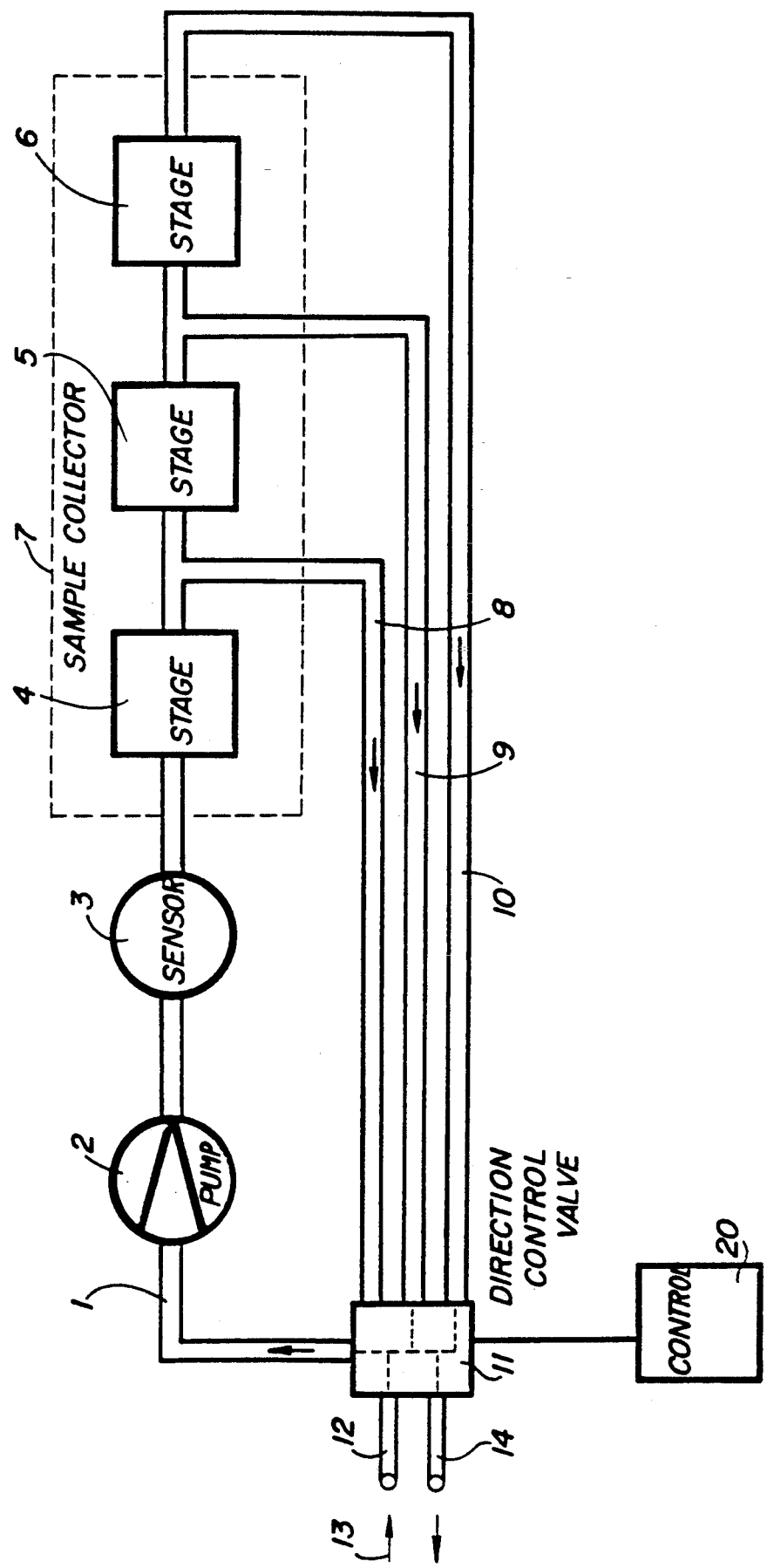

PROCESS AND ARRANGEMENT FOR DETERMINING AT LEAST ONE COMPONENT OF A TEST GAS

BACKGROUND OF THE INVENTION

1. Field of the Invention

This invention relates in general to gas detecting devices and in particular to a new and useful method and apparatus for determining one component of very low concentration of a test gas.

The invention particularly concerns a process for determing one component of very low concentration in a test gas, which is guided in a supply line to concentrate the component across a sample collector, whose amassed quantity of the sample is relinquished to a detection sensor. Furthermore, the invention deals with an arrangement to carry out the process.

In U.S. Pat. No. 4,277,251, on the example of measuring the alcohol content of expired air, a process is employed whereby the breath sample is conveyed through a sample collector, absorbing the alcohol component, and is collected. After the sample is taken, the sample collector is heated, which drives out the absorbed gas and carries it to an attached meter.

However, it is a disadvantage, that during the entire sample collection process of the familiar method, it is not possible to monitor or even measure the gas being investigated for its components. Accordingly, the measurement process is divided into two interdependent successive steps, namely, first the sample collection, during which no measurement can be done, and then the investigation of the sample, during which no new collection can be undertaken. A measuring instrument working with such familiar measurement procedures, therefore, is not capable of measurement during the sample collection. Furthermore, the familiar method is only reliable and informative when the investigated gas contains only one component that is to be detected. For in this case, the material taking up the component in the sample collector and the sensitivity of the measurement instrument can be calibrated against each other. If, however, several components are contained in the test gas, which can be concentrated in the sample collector, then during the subsequent driving off they are all carried to the detection sensor. A separate, component-specific detection of the individual concentrations of individual components are suspected in the test gas. With a collective analysis in the detection sensor, these could produce spurious measurement results by virtue of the socalled cross sensitivity, or the sensitivity of the meter not specific to the type of gas.

SUMMARY OF THE INVENTION

Thus, the invention provides an improved process which, even during the collection of the sample, a measurement signal is present, and that the individual components of a multiple-component test gas not only can be detected, but also a component-specific cross sensitivity of the detection sensor can be controlled.

In accordance with the invention, the test gas is conveyed first across the detection sensor and then across at least one sample collector to separate out at least one component, after which the supply of test gas is interrupted. The separated component is released from the sample collector and taken to the detection sensor, and after interruption of the supply of test gas to the sample collector, the component(s) separated by it are relinquished successively to the detection sensor.

Use of the process enables decomposition of a multicomponent test gas into its components and an individual detection of these, so that cross sensitivities of the detection sensor (as are particularly troublesome in electrochemical or semiconductor sensors, for example) are eliminated and measurement signals specific to the type of gas are obtained. But even during the collection of the sample, the detection sensor can be used to warn of excessively high concentration of one or more gas components.

In an especially simple form, the sample collector comprises an absorption layer, which is cooled during the sample collection step and heated during the component release step. Components that have been simultaneously detained by the absorption layer can be driven off again by heating the collector to the particular specific desorption temperatures and detected individually.

An arrangement for utilization of the process includes at least one sample collector, which is connected behind the detection sensor in the supply line and separates out at least one component of the test gas. A delivery mechanism is provided in series with the sample collector and the detection sensor. The outlet of each particular sample collector is connected across an exit line to the supply line, upstream of the detection sensor. Thus, the detection sensor can be used for measurement and warning during the collection of the sample, and only after the close of the sample collection need each individual collector be connected across its exit line to the detection sensor, so that the sensor produces a component-specific signal. In this way, the initially measured combined signal can be investigated for cross sensitivity of the detection sensor and the concentrations of the individual components can be determined.

It is expedient to bring the exit lines together in a directional control valve, so that they can be connected to or from the supply line, as needed, by a single controller.

An especially favored configuration of the sample collector is as a multistaged unit, whose individual stages for selection of the particular components are arranged in series with the supply line, and can be connected back to the supply line across their own exit lines, parallel to each other, for relinquishing of the selected components.

The multiple stages can be produced by arranging the corresponding absorption layers in a series in a single housing, or several component-specific absorption materials can be intermingled and their absorbed gas components can be separately driven off and taken to the detection sensor by heating to the proper temperatures, for example.

Accordingly, it is an object of the invention to provide an improved apparatus for determining a plurality of gas components which comprises a test passage which has a sensor for detecting a plurality of different gases, and which includes a plurality of separate gas collection stages in the test gas passage, each of the stages having an arrangment for separating a separate gas. Also including a connection to the gas passage permitting separately directing each separated gas component passed the sensor.

A further object of the invention is to provide a method of testing a gas having a plurality of gas components which comprises directing the gas through a test gas passage which includes a sensor and a plurality of separate stages which have separate means for collecting separate components of the gas, and which also includes a connection preventing each stage to be separately passed through the sensor.

A further object of the invention is to provide a process and apparatus for detecting a plurality of separate components of gases which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

While specific embodiments of the invention have been shown and described in detail to illustrate the application of the principles of the invention, it will be understood that the invention may be embodied otherwise without departing from such principles.

BRIEF DESCRIPTION OF THE DRAWINGS

The only figure of the drawings is a schematic diagram showing a device for testing a gas having several components and constructed according to the invention.

DESCRIPTION OF THE PREFERRED EMBODIMENTS

Referring to the drawings in particular, the invention embodied therein comprises a device for determining a plurality of gas components which includes a test gas passage 1 which has a pump 2 therein for advancing a gas to be tested passed a sensor 3, and a sample collector 7 which has stages 1, 2 and 3 and which are designated 4, 5 and 6 in the drawings.

Each of the stages 4, 5 and 6 have separate means for separating a separate gas component. In accordance with the invention, means are connected to the sample collector in the test gas passage for separately directing each separated gas component to the sensor individually. These include the various connecting lines and a direction control valve 11 which is operated by a control 20.

In the diagram, a delivery pump 2, a detection sensor 3, and a sample collecting unit 7 formed of several stages 4, 5 and 6, are connected in sequence within a delivery line 1. The delivery line 1, together with the exit lines 8, 9 and 10 at the individual outlets of the sample collector stages 4, 5 and 6, issues into a directional control valve 11, which is also joined to a connection line 12.

Control of the individual elements is by a controller or control 20, whose control program is switched so that during the collection of the sample the delivery pump 2 carries the test gas through the connection line 12 in the direction of the intake arrow 13 across the sensor 3 and subsequent sample collection stages 1, 2, 3, 4, 5 and 6 and the outlet line 10 back to the directional control valve 11 and from there into a discharge line 14.

During the collection process, the individual components of the test gas are detained in the particular stages 4, 5 and 6, by operation of the control 20 and valve 11, while the sensor 3 measures and displays an aggregate signal from the test gas. After the collection of the sample, the valve 11 is switched so that both the connection line 12 and the discharge line 14 are disconnected from the supply line 1 and the exit lines 8, 9 and 10 are successively connected to the supply line 1 to form individual circuit rings. The individual stages 4, 5 and 6 are then caused to relinquish the collected gas components, which in the case of a stage configured as an absorption layer can be done by the action of heat, whereby the sensor 3 can measure and display a component of the test gas that is separated during the sample collection.

What is claimed is:

1. A process for determining at least on component of lower concentration of a test gas sample using a gas concentration sensor and a sample collector with means for concentrating at least the one component of the test gas, the process comprising the steps of passing the test gas sample across the sensor while obtaining a combined concentration reading of said test gas sample from the sensor; passing the test gas from the sensor to the sample collector to concentrate each of said at least one component therein; interrupting the supply of said test gas to the sensor and separately supplying only each collected component from the sample collector to the sensor and obtaining a component-specific concentration reading therefrom.

2. A process according to claim 1 wherein said sample collector comprises a plurality of stages arranged in series, each stage concentrating a different component of the test gas, further comprising the steps of supplying each collected component sequentially to the sensor and obtaining sequential component-specific concentration readings therefrom corresponding to the concentration of each of said at least one component in said test gas supplied to the sensor.

3. A process according to claim 2 in which each collector stage includes an adsorption layer for one of said at least one component, further comprising the steps of cooling the test sample during its passage across the sensor and to the collector stages and subsequently heating the respective collector stages sequentially for supply of the respective components concentrated therein to the sensor.

4. A device for determining a plurality of gas components from a test sample, comprising means defining a test gas passage, a sensor in said test gas passage for detecting the concentrations of a plurality of different gases in said test gas passage, a plurality of gas collection stages arranged in said test gas passage downstream of the sensor, each stage having means for separating a separate gas component and a separate exit line extending to said test gas passage, a direction control valve located at a connection of said exit lines to said test gas passage, a gas supply inlet line connected to said direction control valve and a discharge line connected to said direction control valve, control means connected to said direction control valve for regulating the connection of said stage exit lines to said test gas passage and said inlet and discharge connections and for directing each separated gas component individually to said sensor separately from each other and from the gas supply.

* * * * *